(12) United States Patent
Aarts (10) Patent No.: US 11,337,659 B2
(45) Date of Patent: May 24, 2022

(54) DETERMINATION SYSTEM FOR DETERMINING A HEART FAILURE RISK

(71) Applicant: KONINKLIJKE PHILIPS N.V., Eindhoven (NL)

(72) Inventor: Ronaldus Maria Aarts, Geldrop (NL)

(73) Assignee: KONINKLIJKE PHILPS N.V., Eindhoven (NL)

( * ) Notice: Subject to any disclaimer, the term of this patent is extended or adjusted under 35 U.S.C. 154(b) by 3 days.

(21) Appl. No.: 16/072,661

(22) PCT Filed: Jan. 16, 2017

(86) PCT No.: PCT/EP2017/050738
§ 371 (c)(1),
(2) Date: Jul. 25, 2018

(87) PCT Pub. No.: WO2017/129426
PCT Pub. Date: Aug. 3, 2017

(65) Prior Publication Data
US 2019/0083043 A1    Mar. 21, 2019

(30) Foreign Application Priority Data
Jan. 28, 2016    (EP) .................................... 16153222

(51) Int. Cl.
*A61B 5/00* (2006.01)
*A61B 5/021* (2006.01)
(Continued)

(52) U.S. Cl.
CPC ........ *A61B 5/7275* (2013.01); *A61B 5/02116* (2013.01); *A61B 5/02416* (2013.01);
(Continued)

(58) Field of Classification Search
None
See application file for complete search history.

(56) References Cited

U.S. PATENT DOCUMENTS 6,942,622 B1    9/2005    Turcott
2003/0074029 A1    4/2003    Deno et al.
(Continued)

FOREIGN PATENT DOCUMENTS

EP    1302156 A2    4/2003
EP    2786704 A1    10/2014
WO    2004098381 A2    11/2004

OTHER PUBLICATIONS

Sinnecker, Daniel, et al. "Postextrasystolic Blood Pressure Potentiation Predicts Poor Outcome of Cardiac Patients." Journal of the American Heart Association, vol. 3, No. 3, 2014, pp. 1-10., doi:10.1161/jaha.114.000857 (Year: 2014).*

(Continued)

*Primary Examiner* — Gary Jackson
*Assistant Examiner* — Anant A Gupta (57) ABSTRACT

The invention relates to a determination system for determining a heart failure risk for a subject (4). The determination system (1) comprises a photoplethysmogram providing unit for providing a photoplethysmogram of the subject and a heart failure risk determination unit for determining the heart failure risk based on the provided photoplethysmogram. A photoplethysmogram can be provided in an unobtrusive way by using a photoplethysmogram sensor without requiring a physician's attendance. In particular, it is not necessarily required to measure electrocardiograms, to carry out blood tests and to perform a coronary angiography for determining the heart failure risk. The heart failure risk can therefore be determined in a technically relatively simple way without requiring a physician's attendance.

22 Claims, 6 Drawing Sheets

(51) Int. Cl.
*A61B 5/024* (2006.01)
*A61B 5/11* (2006.01)
*A61B 5/1455* (2006.01)
*G16H 50/30* (2018.01)
*G16H 50/20* (2018.01)
*G16H 40/63* (2018.01)
*A61B 5/08* (2006.01)

(52) U.S. Cl.
CPC ........ *A61B 5/1118* (2013.01); *A61B 5/14551* (2013.01); *A61B 5/681* (2013.01); *A61B 5/7278* (2013.01); *G16H 40/63* (2018.01); *G16H 50/20* (2018.01); *G16H 50/30* (2018.01); *A61B 5/0816* (2013.01)

(56) References Cited

U.S. PATENT DOCUMENTS

| | | |
|---|---|---|
| 2010/0049060 A1 | 2/2010 | Schecter |
| 2009/0576453 | 4/2010 | Yi et al. |
| 2010/0087890 A1* | 4/2010 | Wariar ................ A61N 1/3627 607/27 |
| 2010/0094102 A1 | 4/2010 | Zhang et al. |
| 2010/0234906 A1* | 9/2010 | Koh .................... A61N 1/3627 607/3 |
| 2011/0152957 A1 | 6/2011 | Shaquer |
| 2011/0201953 A1 | 8/2011 | Kaiser et al. |
| 2011/0208016 A1 | 8/2011 | Bombardini |
| 2012/0173470 A1 | 7/2012 | Bashour et al. |
| 2013/0060297 A1 | 3/2013 | Stein |
| 2014/0316286 A1* | 10/2014 | Addison ................ A61B 6/504 600/484 |
| 2014/0358012 A1* | 12/2014 | Richards .............. A61B 5/6802 600/479 |
| 2015/0065826 A1* | 3/2015 | Mulligan ............. A61B 5/7267 600/323 |
| 2015/0289777 A1 | 10/2015 | Linker |
| 2015/0342492 A1 | 12/2015 | Thakur et al. |
| 2016/0192890 A1* | 7/2016 | Averina ................ A61B 5/1118 600/481 |
| 2017/0027474 A1* | 2/2017 | Sharma ................ A61B 5/0537 |
| 2017/0156680 A1 | 6/2017 | Barretto et al. |
| 2019/0076031 A1* | 3/2019 | Valys .................... A61B 5/361 |

OTHER PUBLICATIONS

Sinnecker, et al., "Postextrasystolic Blood Pressure Potentiation Predicts Poor Outcome of Cardiac Patients", Journal of the American Heart Association, vol. 3, No. 3, Jun. 3, 2014, pp. 1-10.

Cooper, Wayne M., "Postextrasystolic Potentiation Do We Really Know What it Means and How to Use It?" Potentiation, Force-Frequency, Contractility, Downloaded from http://cir.ahajournals.org/ by guest on Oct. 14, 2015, pp. 2962-2971.

Cernat, et al., "Real-time extraction of the respiratory rate from photoplethysmographic signals using wearable devices", Faculty of Medical Engineering, University of Politehnica of Bucharest, Romania (Abstract).

Cooper, et al., "Postextrasystolic Potentiation and Echocardiography—The Effect of Varying Basic Heart Rate, Extrasystolic Coupling Interval and Postextrasystolic Interval", Pesp and Echocardiography, vol. 66, No. 4, Oct. 1982, pp. 771-776.

* cited by examiner

DETERMINATION SYSTEM FOR DETERMINING A HEART FAILURE RISK

This application is the U.S. National Phase application under 35 U.S.C. § 371 of International Application No. PCT/EP2017/050738, filed on Jan. 16, 2017, which claims the benefit of European Application Serial No. 16153222.1, filed Jan. 28, 2016. These applications are hereby incorporated by reference herein.

FIELD OF THE INVENTION

The invention relates to a determination system, a determination method and a computer program for determining a heart failure risk for a subject.

BACKGROUND OF THE INVENTION

U.S. Pat. No. 6,942,622 B1 discloses a method for monitoring the progression of a disease state of a patient. A pulse amplitude signal indicative of cardiac contraction of the patient's heart is sensed, amplitude changes within the sensed signal over time are identified, and a measure of autonomic tone is calculated based on the identified amplitude changes. These steps are repeated, in order to acquire a plurality of autonomic tone measures, wherein the plurality of tone measures are analyzed for providing an indication of the progression of the disease state of the patient.

The article "Utility of Second Derivative of the Finger Photoplethysmogram for the Estimation of the Risk of Coronary Heart Disease in the General Population" by T. Otsuka et al., Circulation Journal, volume 70, pages 304 to 310 (2006) discloses a method for determining a measure for an increased arterial stiffness which is associated with coronary heart disease. In particular, it is suggested to measure the second derivative of a finger photoplethysmogram for measuring the increased arterial stiffness.

EP 1 302 156 A2 discloses a monitor for assessing a heart failure status of a patient. The monitor comprises a light source and a light detector adapted to produce a photoplethysmogram signal that is representative of arterial pulse pressure. The monitor further comprises a means for assessing the heart failure status based on the shape of the photoplethysmogram signal.

US 2010/0049060 A1 discloses an implantable system including an implantable photoplethysmogram sensor, wherein the implantable system is used for obtaining an arterial photoplethysmogram waveform and determining a surrogate of cardiac afterload by determining a metric of a terminal portion of the arterial photoplethysmogram waveform, wherein the terminal portion is from a maximum of the arterial photoplethysmogram waveform to a following minimum of the photoplethysmogram waveform.

Heart failure (HF), which may also be referred to as a congestive heart failure, chronic heart failure or congestive cardiac failure, describes a situation in which the heart is unable to pump sufficiently to maintain blood flow to meet the needs of a subject's body. The risk of getting such a HF can be determined based on electrocardiograms (ECGs), blood tests and coronary angiography. These techniques for determining the HF risk are relatively complex and need to be carried out by a physician such that generally they are not carried out many times and especially not continuously. This often leads to a too late awareness of a significant risk of getting HF.

SUMMARY OF THE INVENTION

It is an object of the present invention to provide a determination system, a determination method and a computer program for determining a HF risk for a subject, which allow for a determination of the HF risk in a technically relatively simple way which does not necessarily require a physician's attendance.

In a first aspect of the present invention a determination system for determining a HF risk for a subject is presented, wherein the determination system comprises:
 a photoplethysmogram (PPG) providing unit for providing a PPG of the subject,
 a HF risk determination unit for determining a HF risk based on the provided PPG, wherein the heart failure risk determination unit is adapted to detect at least one of a presence of a postextrasystolic potentiation (PESP) and a disturbed force-frequency relation (FFR) based on the provided photoplethysmogram and to determine the heart failure risk based on the detection of the at least one of the presence of the postextrasystolic potentiation and the disturbed force-frequency relation.

A PPG can be provided in an unobtrusive way by using a PPG sensor without requiring a physician's attendance. In particular, it is not necessarily required to measure ECGs, to carry out blood tests and to perform a coronary angiography for determining the HF risk. The HF risk can therefore be determined in a technically relatively simple way without requiring a physician's attendance.

The PPG providing unit can be a storing unit, in which the PPG is stored already, wherein the PPG providing unit can be adapted to provide the stored PPG. However, the PPG providing unit can also be a receiving unit for receiving a PPG from a PPG measurement unit and for providing the received PPG. Moreover, the PPG providing unit can be the PPG measurement unit itself, wherein the PPG providing unit provides the measured PPG. The PPG measurement unit preferentially comprises one or more light sources for illuminating a part of the subject's body and one or several detectors for detecting the light from the subject's body, wherein the PPG measurement unit is preferentially adapted to determine the PPG based on the detected light. In a preferred embodiment the PPG measurement unit is a pulse oximeter.

The heart failure risk determination unit can be adapted to determine the temporal behavior of characteristics of the left ventricular pressure based on the PPG, to provide rules defining the HF risk depending on the determined temporal behavior, and to determine the HF risk based on the determined temporal behavior and the provided rules. The rules can define how the presence of the PESP and/or a disturbance of a force-frequency relation can be detected based on the temporal behavior of characteristics of the left ventricular pressure. For instance, the HF risk determination unit can be adapted to determine peak values for different times, which are indicative of the heights of the peaks of the left ventricular pressure over time, for determining the temporal behavior. The rules can define the detection of a presence of the PESP and/or a disturbance of the force-frequency relation based on an abnormal temporal behavior of the peak values, which indicates a relatively high risk of getting a HF. It should be understood that the expressions "at least one of A and B" and "A and/or B" include a) A without B, b) B without A, and c) A and B.

In an embodiment the HF risk determination unit is adapted to provide rules which include a first peak value threshold and a second peak value threshold and which define the detection of the presence of the PESP depending on whether a) a peak value is smaller than the first peak value threshold and b) the following peak value is not larger than the second peak value threshold. In particular, the HF risk determination unit is adapted to provide rules which define that the HF risk is larger, if a peak value is smaller than the first peak value threshold and the following peak value is not larger than the second peak value threshold, and smaller, if a peak value is smaller than the first peak value threshold and the following peak value is larger than the second peak value threshold. In a healthy heart a peak value, which is smaller than the first peak value threshold, can relate to a so called "ineffective beat" and the following peak value, which is larger than the second peak value threshold, can relate to a so called "potentiated beat". This ineffective beat and the following potentiated beat can indicate the PESP of a healthy heart. If this behavior is not present, i.e. if an ineffective beat is not followed by a potentiated beat, this can indicate a relatively high risk of getting a HF.

In an embodiment the heart failure risk determination unit is adapted to determine frequency values for different times, which are indicative of the frequency of the left ventricular pressure over time, for determining the temporal behavior. The rules can define which temporal behavior of the frequency of the left ventricular pressure indicates a relatively high risk of getting a HF, wherein these rules can be used together with the frequency values for determining the HF risk. For instance, the HF risk determination unit can be adapted to provide rules which define the detection of the disturbed force frequency relation depending on whether the frequency values increase over time, while the peak values do not increase over time. In particular, the HF risk determination unit can be adapted to provide rules which define that the HF risk is larger, if the frequency values increase over time, while the peak values do not increase over time, and smaller, if the frequency values increase over time, while the peak values increase over time. This allows reliably using the force-frequency relation for determining the HF risk. In a healthy heart having a normal force-frequency relation the height of the peaks of the left ventricular pressure increases, if the frequency of the left ventricular pressure increases. If this healthy behavior of the heart is not observed, the risk of getting a HF can be relatively high and this can be used by the HF risk determination unit for determining the HF risk.

The temporal behavior of characteristics of the left ventricular pressure can be similar to the temporal behavior of corresponding characteristics of the PPG. Thus, for instance, peak values, which are indicative of the heights of the peaks of the left ventricular pressure, and their temporal positions may be determined by determining peak values of the PPG, wherein known extraction techniques may be used like the techniques generally used for detecting peaks in an ECG.

The determination system can further comprise an activity state providing unit for providing an indication of the activity state of the subject, wherein the HF risk determination unit can be adapted to provide rules including an activity frequency threshold that depends on the activity state and defining the HF risk depending on whether the frequency values are larger than the activity frequency threshold for the respective activity state. In particular, the HF risk determination unit can be adapted to provide rules defining that the HF risk is larger, if the frequency values are larger than the activity frequency threshold for the respective activity state, and smaller, if the frequency values are smaller than the activity frequency threshold for the respective activity state. Thus, in addition to the detection of at least one of a presence of a PESP and a disturbed force-frequency relation, the indication of the activity state can be used for determining the HR risk. By also considering the activity state of the subject, for instance, whether the subject is resting, especially sleeping, or walking, the accuracy of determining the HF risk can be further improved. In particular, it can be considered that, if the frequency is relatively high and the subject is resting, this may indicate a relatively high HF risk, whereas, if the frequency is relatively high and the subject is walking or running, the relatively high frequency does not indicate a relatively large risk of getting a HF.

In an embodiment the HF risk determination unit is adapted to provide rules which include a frequency deviation threshold and which define the HF risk depending on whether a deviation between temporally consecutive frequency values is larger than the frequency deviation threshold. In particular, the HF risk determination unit can be adapted to provide rules which define that the HF risk is larger, if a deviation between temporally consecutive frequency values is larger than the frequency deviation threshold, and smaller, if a deviation between temporally consecutive frequency values is smaller than the frequency deviation threshold. Thus, in addition to the detection of at least one of a presence of a PESP and a disturbed FFR, a comparison of a) a deviation between temporally consecutive frequency values and b) a frequency deviation threshold can be used for determining the HR risk. A frequency value, which may be defined by the inverse of the temporal distance between two consecutive peaks and hence which is indicative of the temporal distance between two consecutive peaks, can indicate the degree of regularity of the heart beat. If the changes between temporally consecutive frequency values are larger than the frequency deviation threshold, this can indicate a relatively large irregularity in the heart beat and hence atrial fibrillation (AF). If AF is detected, the risk of getting a HF can be relatively large, wherein this knowledge can be used by the HF risk determination unit for determining the HF risk.

In an embodiment the HF risk is binary, i.e. the HF risk determination unit can be adapted to determine either that the HF risk is zero or relatively small or that the HF risk is relatively large. This can be regarded as assigning the subject to one of two degrees of HF risk. The HF risk determination unit can also be adapted to determine to which degree of more than two degrees of HF risk the subject needs to be assigned based on the provided PPG.

The above mentioned rules can be combined for determining the HF risk. In particular, the HF risk determination unit can be adapted to provide rules defining the HF risk depending on at least one of a) whether the temporal behavior of the characteristics of the left ventricular pressure indicates that an ineffective beat is followed by a potentiated beat and b) whether the temporal behavior of the characteristics of the left ventricular pressure indicates that the peak values of the peaks of the left ventricular pressure increase when the frequency of the left ventricular pressure increases, wherein the rules can optionally further define the HF risk depending on at least one of c) the change of the frequency of the left ventricular pressure depending on the activity state and d) the deviation between temporally consecutive frequency values. The HF risk determination unit can also be adapted to provide rules defining the HF risk depending on further temporal behaviors of the characteristics of the left ventricular pressure.

It is preferred that the determination system comprises a breathing rate providing unit for providing the breathing rate of the subject, wherein the HF risk determination unit is adapted to determine the HF risk also based on the provided breathing rate. In particular, the provided rules can define the HR risk not only based on the temporal behavior of the characteristics of the left ventricular pressure, but also based on the breathing rate. This can lead to a further improved accuracy of determining the HF risk.

In an embodiment the determination system comprises an activity state providing unit for providing an indication of the activity state of the subject, wherein the HF risk determination unit can be adapted to provide a breathing rate threshold that depends on the activity state and to determine the HF risk also depending on whether the breathing rate is larger than the breathing rate threshold for the respective activity state. By also considering the activity state of the subject, for instance, whether the subject is resting, especially sleeping, or walking, the accuracy of determining the HF risk can be further improved. In particular, it can be considered that, if the breathing rate is relatively high and the subject is resting, this may indicate a relatively high HF risk, whereas, if the breathing rate is relatively high and the subject is walking or running, the relatively high breathing rate does not indicate a relatively high risk of HF.

Preferentially the breathing rate providing unit is adapted to determine the breathing rate based on the PPG and to provide the determined breathing rate. This allows determining the breathing rate without requiring an additional device like a chest belt or a flow sensor, thereby allowing for the provision of the breathing rate in a very unobtrusive way.

In another aspect of the present invention a determination method for determining a HF risk for a subject is presented, wherein the determination method comprises:

providing a PPG of the subject by a PPG providing unit,
determining a HF risk based on the provided PPG by a HF risk determination unit, wherein the heart failure risk determination unit detects at least one of a presence of a postextrasystolic potentiation and a disturbed force-frequency relation based on the provided photoplethysmogram and determines the heart failure risk based on the detection of the at least one of the presence of the postextrasystolic potentiation and the disturbed force-frequency relation.

In a further aspect of the present invention a computer program for determining a HF risk for a subject is presented, the computer program comprising program code means for causing a determination system as defined in claim 1 to carry out the determination method as defined in claim 14, when the computer program is run on the determination system.

It shall be understood that the determination system of claim 1, the determination method of claim 14, and the computer program of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
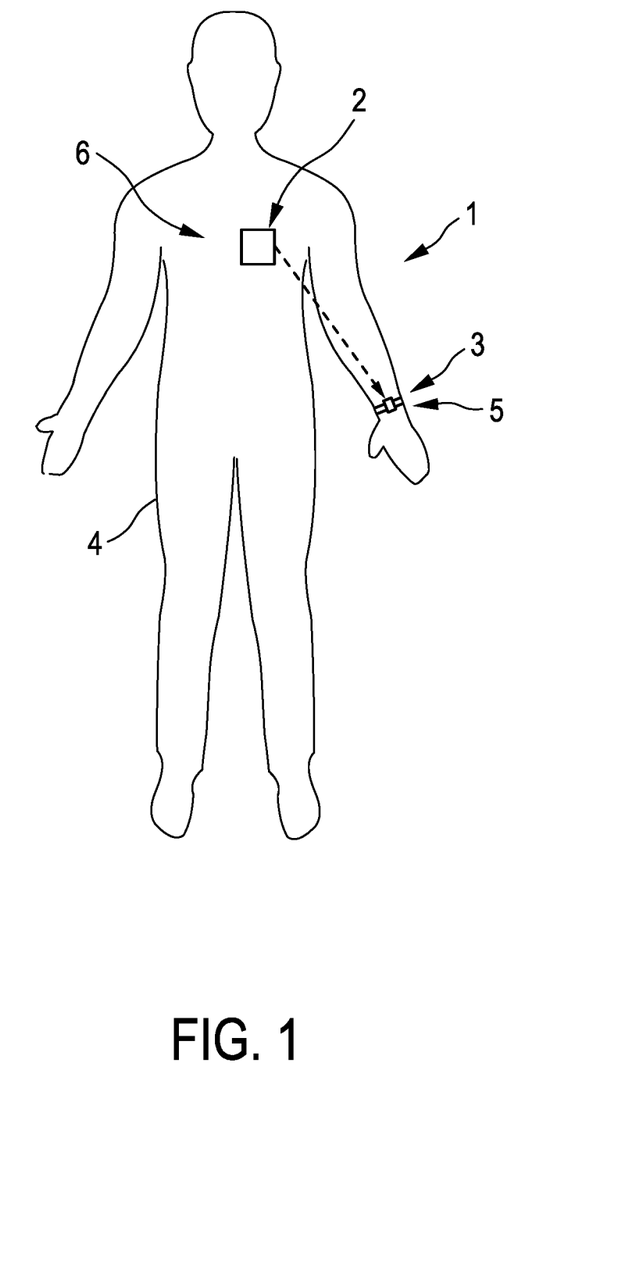
FIG. 1 shows schematically and exemplarily a person with an embodiment of a determination system for determining a HF risk.

FIG. 1 shows schematically and exemplarily a person 4 wearing an embodiment of a determination system 1 for determining a HF risk. The detection system 1 comprises an accelerometer 2 attached to the chest 6 of the person 4 and a watch-like device 3 to be worn at the wrist 5 of the person 4. In other embodiments the accelerometer 2 can also be attached to another part of the person 4. Moreover, instead of a watch-like device 3 to be worn at the wrist 5 of the person 4, this device can be attached to another part of the person 4 and may not be watch-like. For instance, this device can also be an ear-in device.

Figure 2:
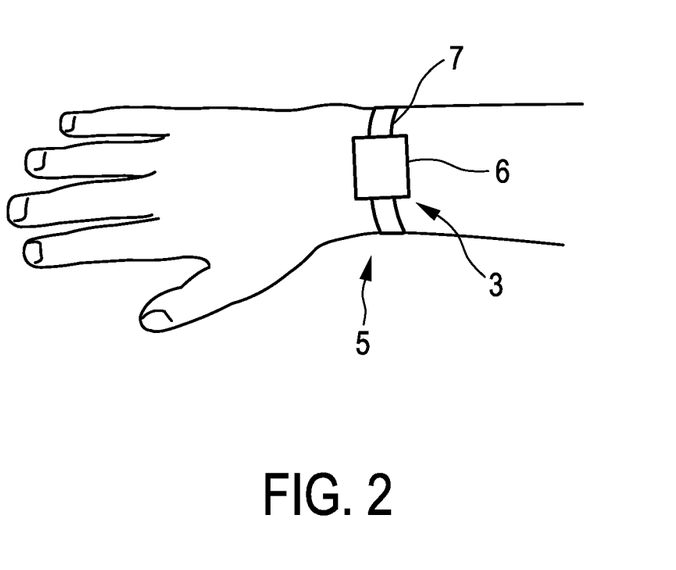
FIG. 2 shows schematically and exemplarily a watch-like device of the determination system shown in FIG. 1.

The watch-like device 3 comprises a casing 6 held at the wrist 5 by a wrist band 7 as schematically and exemplarily illustrated in FIG. 2. As schematically and exemplarily illustrated in FIGS. 3 and 4, the watch-like device 3 comprises a communication unit 8 and the accelerometer 2 comprises a corresponding communication unit 14, which allow the watch-like device 3 and the accelerometer 2 to communicate to each other. The accelerometer 2 further comprises an acceleration sensor 13 for measuring an acceleration of the person 4, wherein the measured acceleration is communicated via the communication units 8, 14 from the accelerometer 2 to the watch-like device 3. The acceleration provided by the acceleration sensor 13 is indicative of the activity state of the person 4 such that the acceleration sensor 13 can be regarded as being an activity state providing unit for providing an indication of the activity state. For instance, the measured acceleration can indicate whether the person 4 is resting, especially sleeping, or whether the person 4 is walking or running.

Figure 3:
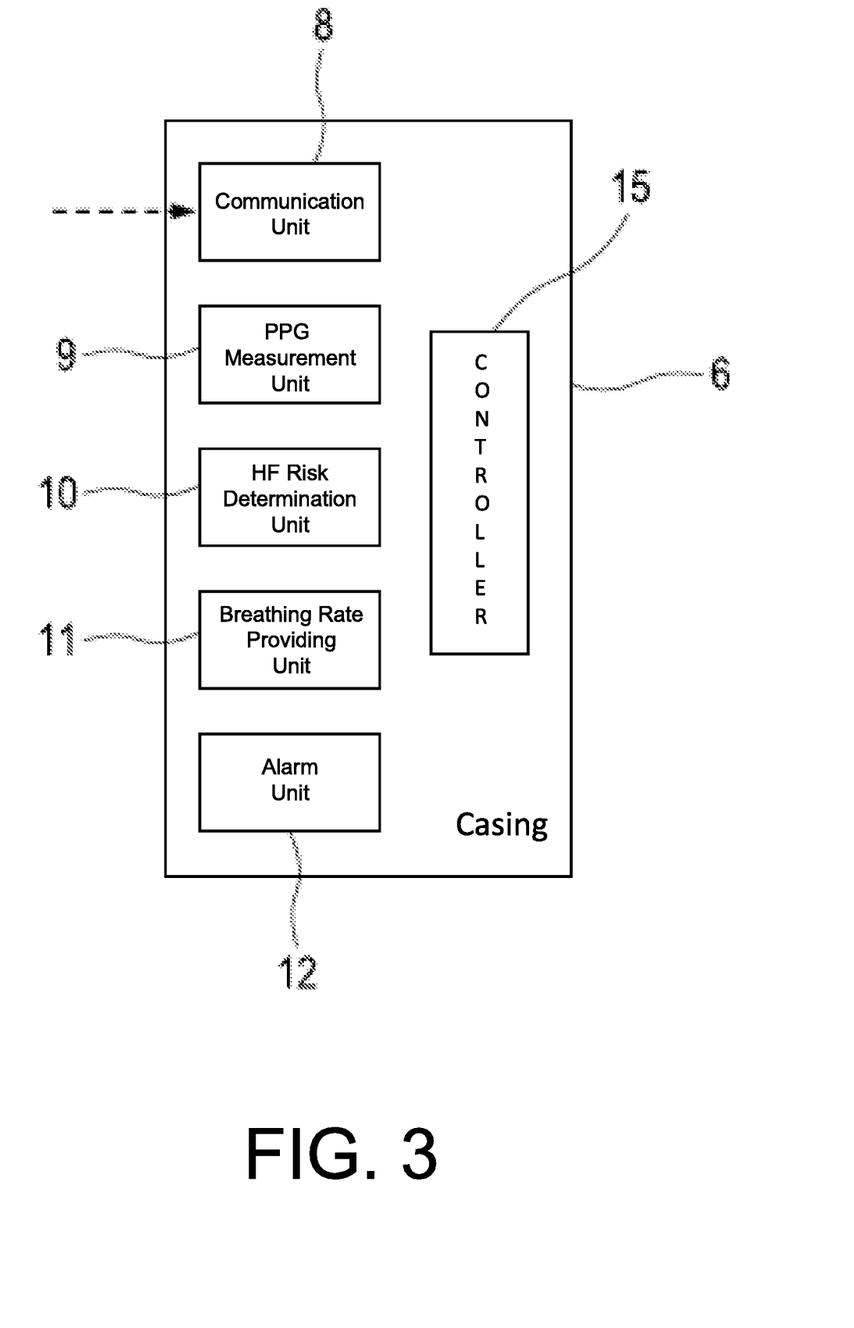
FIG. 3 shows schematically and exemplarily several components of the watch-like device shown in FIG. 2 in more detail.

The casing 6 of the watch-like device 3 further comprises a PPG measurement unit for measuring a PPG. The PPG measurement unit 9 can be a known PPG measurement unit, which comprises light-emitting diodes (LEDs) directing light into the skin of the person 4 at the wrist 5 and which detects light from the skin at the wrist 5, wherein the PPG measurement unit 9 generates the PPG based on the detected light. In this embodiment the PPG measurement unit 9 is a pulse oximeter. The measured PPG is provided to a HF risk determination unit 10 for determining a HF risk based on the provided PPG. Since the PPG measurement unit 9 provides the measured PPG, the PPG measurement unit 9 can also be regarded as being a PPG providing unit.

The casing 6 of the watch-like device 3 further includes a breathing rate providing unit 11 for providing the breathing rate of the person 4 based on the PPG measured by the PPG measurement unit 9, wherein the determined breathing rate is also provided to the HF risk determination unit 10. For extracting the breathing rate from the PPG known breathing rate extraction techniques can be used like the extraction technique disclosed in the article "Real-time extraction of the respiratory rate from photoplethysmographic signals using wearable devices" by R. A. Cernat, C. Ungureanu, G. M. Ungureanu, R. Aarts and J. Arends, Workshop on Smart Healthcare and Healing Environments in conjunction with AMI '14, European Conference on Ambient Intelligence, Eindhoven, The Netherlands, Nov. 11 to 13, 2014, which is also published in Springer's Lecture Notes in Computer Science and which is herewith incorporated by reference.

The HF risk determination is adapted to determine the temporal behavior of characteristics of the left ventricular pressure based on the PPG and to provide rules defining the HF risk depending on the determined temporal behavior and optionally also depending on the breathing rate, wherein the HF risk determination unit is further adapted to determine the HF risk based on a) the provided rules and b) the determined temporal behavior and optionally the breathing rate. In particular, the HF risk determination unit is adapted to determine peak values for different times, which are indicative of the heights of the peaks of the left ventricular pressure over time, and to determine frequency values for different times, which are indicative of the frequency of the left ventricular pressure over time, for determining the temporal behavior. Moreover, the HF risk determination unit is adapted such that the provided rules define a first peak value threshold, a second peak value threshold, an activity frequency threshold, a frequency deviation threshold and a breathing rate threshold. The HF risk determination unit is adapted to provide the rules such that they define the HF risk depending on at least one of a) whether a peak value is smaller than the first peak value threshold and the following peak value is not larger than the second peak value threshold, i.e. based on a detection of a presence of PESP, and b) whether the peak values do not increase while the frequency values increase, i.e. based on a detection whether a force-frequency relation is disturbed, and optionally further depending on at least one of c) whether a deviation between temporally consecutive frequency values is larger than the frequency deviation threshold, d) whether the frequency values are larger than the activity frequency threshold for the respective activity state, and e) whether the breathing rate is larger than the breathing rate threshold for the respective activity state.

Figure 4:
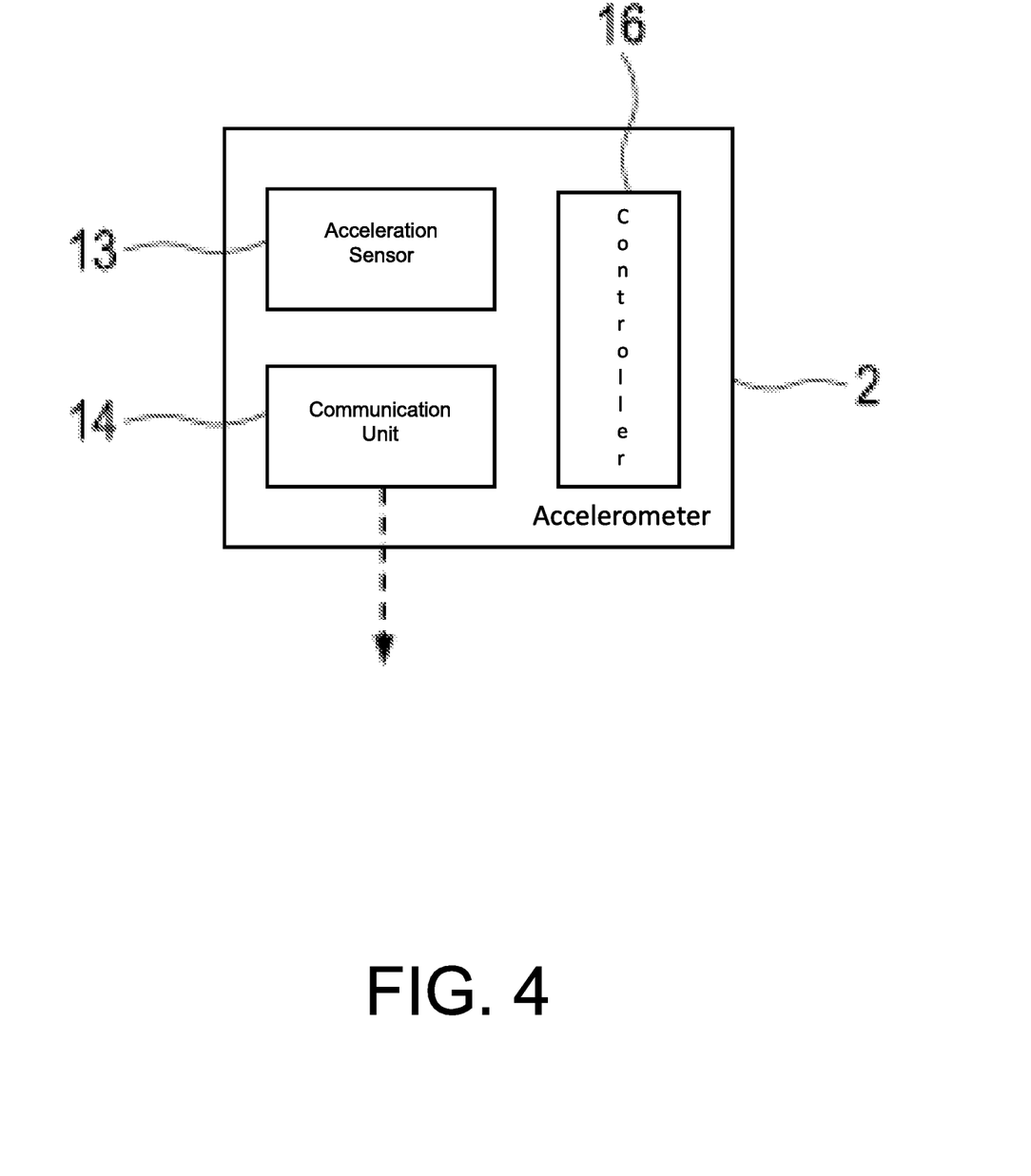
FIG. 4 shows schematically and exemplarily an accelerometer of the determination system shown in FIG. 1 in more detail.

In this embodiment the rules define two degrees of HF risk only, wherein a first degree indicates that the HF risk is zero or relatively small and a second degree indicates a relatively large HF risk. If the HF risk determination results in the second degree, an alarm unit 12 generates an alarm, which might be optical and/or acoustical and/or tactile, in order to indicate that the second degree of HF risk has been determined. The components of the watch-like device are controlled by a controller 15. Also the accelerometer 2 comprises a controller 16 for controlling the components of the accelerometer.

The rules can be predefined or they can be learned from a patient during use. For instance, the rules can be determined based on measurements performed at a population of patients, wherein it is known which of these patients have which degree of HF risk. Rules can also be obtained from literature, for instance, from the article "Postextrasystolic Blood Pressure Potentiation Predicts Poor Outcome of Cardiac Patients" by D. Sinnecker et al., Journal of the American Heart Association, 2014, which is herewith incorporated by reference.

The rules can define that the first degree of HF risk is present, if none of the above mentioned conditions used by the HF risk determination unit for determining the HF risk is fulfilled. The HF risk determination unit can further be adapted to determine that the second degree of HF risk is present, if at least one of these conditions is fulfilled. In an embodiment the HF risk determination unit can be adapted to determine a HF risk from a larger group of degrees of HF risk, which comprises more than two degrees, i.e. in an embodiment the HF risk is not binary. For instance, if none of the above mentioned conditions is fulfilled, the HF risk determination unit can determine the smallest degree of HF risk. If all conditions are fulfilled, the HF determination unit can determine the largest degree of HF risk. The rules can further define intermediate degrees of HF risks, which correspond to situations, in which some, but not all, of the conditions are fulfilled.

The PPG measurement unit 9 is preferentially adapted to provide the PPG continuously in realtime. Moreover, also the acceleration sensor 13 is preferentially adapted to provide the acceleration of the person 4 in realtime. This allows the breathing rate providing unit 11 to continuously provide the breathing rate in realtime and the HF risk determination unit 10 to determine the respective degree of HF risk also in realtime. The HF risk can therefore be continuously monitored and, if necessary, an alarm can be generated.

Figure 5:
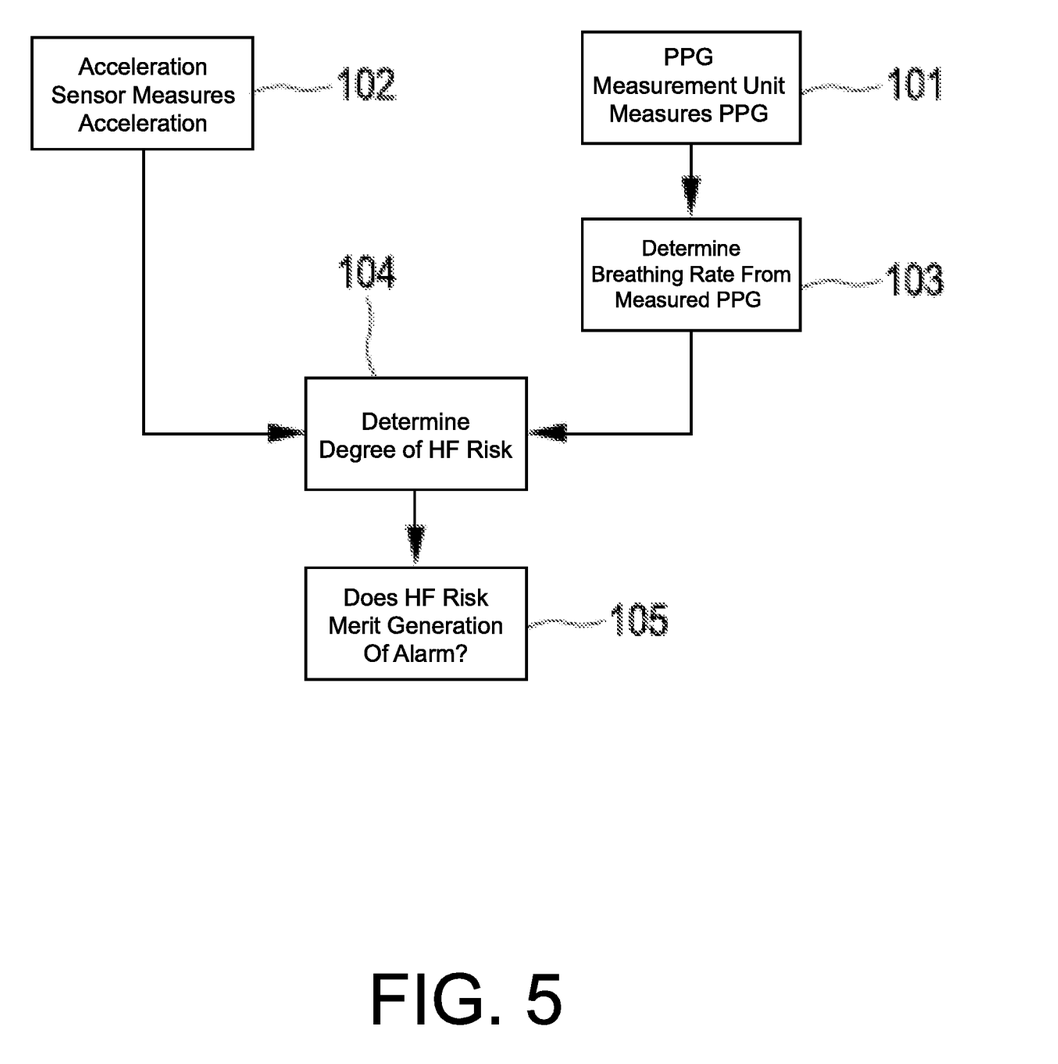
FIG. 5 shows a flowchart exemplarily illustrating an embodiment of a determination method for determining a HF risk, FIG. 6 exemplarily illustrates ventricular pressure over time for a resting person, FIG. 7 exemplarily illustrates ventricular pressure over time showing PESP, and FIG. 8 exemplarily illustrates ventricular pressure over time for a non-resting person.

In the following an embodiment of a determination method for determining a HF risk of the person 4 will exemplarily be described with reference to a flowchart shown in FIG. 5.

In step 101 the PPG measurement unit 9 measures a PPG and in step 102 the acceleration sensor 13 measures the acceleration. In step 103 the breathing rate providing unit 11 determines the breathing rate based on the measured PPG and in step 104 the HF risk determination unit determines the degree of HF risk based on the measured acceleration, the determined breathing rate and the PPG. In step 105 it is determined whether the degree of HF risk suffices the generation of an alarm or not, wherein in the first case the alarm unit 12 generates an alarm. For instance, if the lowest degree of HF risk, which indicates a HF risk of zero or only a very small HF risk, has been determined in step 104, an alarm may not be generated in step 105, wherein, if a large degree of HF risk has been determined, an alarm may be generated.

A HF occurs when the heart is unable to pump sufficiently to maintain blood flow to meet the body's needs. Signs and symptoms can include shortness of breath, excessive tiredness and leg swelling. The shortness of breath can be worse with exercise, but can also be present while lying down and may even wake the person at night. Causes of HF include coronary artery disease including a previous myocardial infarction, high blood pressure, AF, valvular heart disease, excessive alcohol use, infection, cardiomyopathy of an unknown cause, et cetera. The HF may be caused by changing either the structure or the functioning of the heart. Myocardial infarction, especially acute myocardial infarction, occurs when blood flow stops to a part of the heart causing damage to the heart muscle. AF is an abnormal heart rhythm characterized by rapid and irregular beating. AF can start as brief periods of abnormal beating which become longer and possibly constant over time.

Figure 6:
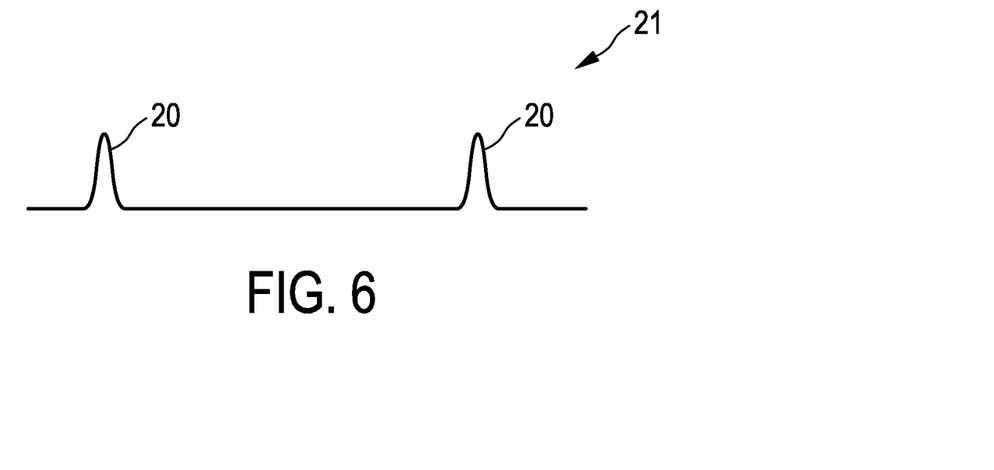
Figure 7:
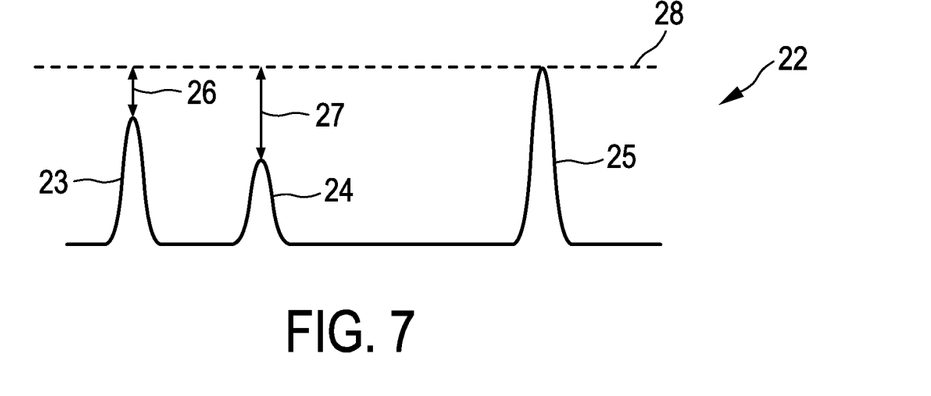

PESP includes an increase in contractility that follows an extra systole. PESP is independent of muscle loading and represents a distinct property of the myocardium. FIG. 6 schematically and exemplarily shows the ventricular pressure 21 with peaks 20 without PESP in a rest situation. FIG. 7 shows the ventricular pressure 22 of a person with normal PESP. If PESP is present, after a heart beat 23 an ineffective beat 24 follows, wherein the ineffective beat 24 is followed by a potentiated beat 25. In FIG. 7 the height of the peak 25 is indicated by line 28 and the height differences between the peaks 23, 24 and the peak 25 are indicated by double arrows 26, 27, respectively. In an embodiment the height difference 26 and/or the height difference 27 may be used for determining the heart failure risk. For instance, the heart failure risk determination unit can be adapted to provide rules which include a first peak value threshold and a second peak value threshold and which define the heart failure risk depending on whether a) a peak value of a peak 24 is smaller than the first peak value threshold and b) a peak value of a following peak 25 is not larger than the second peak value threshold. The heart failure risk determination unit can also be adapted to provide rules which consider peaks only at certain temporal positions defined by a given frequency, i.e. by considering peaks only, which correspond to the given frequency. The frequency is preferentially given by previous waves of the PPG. For instance, previous PPG waves can correspond to the left ventricular pressure shown in FIG. 6 having a certain frequency. In FIG. 7 peaks 23 and 25 correspond to this frequency such that these peaks 23, 25 may be used for determining the HF risk. In particular, the rules can include a third peak value threshold and a fourth peak value threshold and define the HF risk depending on whether a) the peak value of the peak 23 is smaller than the third peak value threshold and b) the peak value of the following peak 25 is not larger than the fourth peak value threshold.

Figure 8:
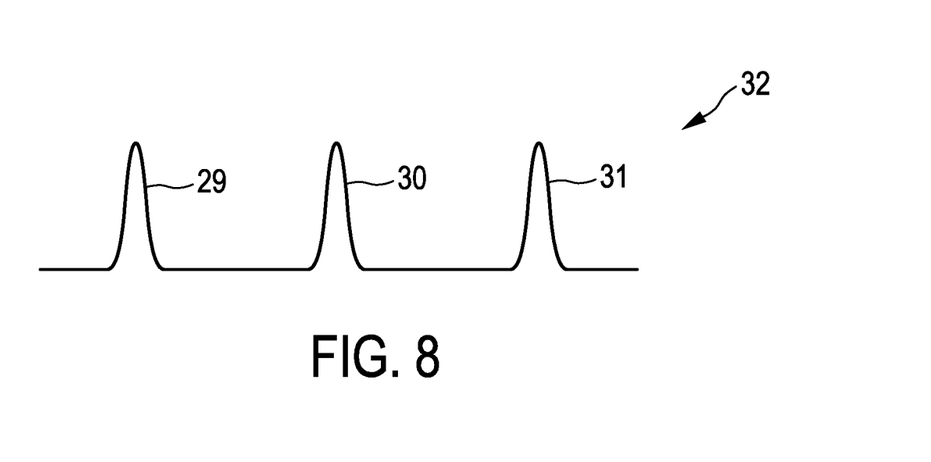

FIG. 8 shows the ventricular pressure 32 of a person with a normal force-frequency relation, i.e. in comparison to FIG. 6 the peak values indicating the heights of the peaks 29, 30, 31 are larger and the frequency is also larger. Hence, the HF risk determination unit can be adapted to provide rules which define the HF risk depending on whether the frequency values increase over time, while the peak values do not increase over time. In particular, the HF risk determination unit can be adapted to provide rules which define that the HF risk is larger, if the frequency values increase over time, while the peak values do not increase over time, and smaller, if the frequency values increase over time, while the peak values increase over time.

The PPG, which is preferentially measured 24 hours a day by using the watch-like device, can be regarded as being a surrogate measure for the ventricular pressure illustrated in FIGS. 6 to 8. The PPG signal can also be used to detect AF. Preferentially, the HF refers to a myocardial infarction such that the HF risk determination unit is preferentially adapted to determine the risk of myocardial infarction.

Although in an above described embodiment the breathing rate is determined based on the PPG, in other embodiments an extra breathing rate sensor can be used for providing the breathing rate. For instance, a chest belt or a flow sensor may be used for determining the breathing rate. The breathing rate can be used to detect shortness of breath and it can be detected whether this shortness of breath is correlated with physical activity measured by the accelerometer, in order to determine the HF risk.

The PESP and force-frequency relationships are disturbed in patients who have a relatively high HF risk, wherein these disturbances can be detected with a single device like the above mentioned watch-like device with the PPG measurement unit or an in-ear device with a PPG measurement unit. In particular, the HF risk determination unit can be adapted to detect at least one of PESP and a force-frequency relation and optionally also AF of the subject's heart based on the provided PPG and to determine the HF risk based on the detection of the at least one of the PESP and the force-frequency relation and optionally the AF. The HF risk determination unit can be adapted to detect the at least one of PESP and a force-frequency relationship and optionally AF of the subject's heart based on the determined temporal behavior of characteristics of the left ventricular pressure obtained from the PPG.

The PPG is preferentially measured by using an unobtrusive measuring device like the above mentioned watch-like device or an in-ear device with a PPG sensor, i.e. with a PPG measurement unit. The HF risk determination unit can be adapted to detect an irregularity during PESP or in other situations. The HF risk determination unit can also be adapted to detect AF as irregularity or other irregularities.

The HF risk determination unit is preferentially adapted to determine the HF risk without using baselines, i.e. data of the person measured, for instance, at the beginning of the monitoring process. Preferentially, the HF risk determination unit is adapted to determine the HF risk based on several currently measured PPG waves. In this regard the HF risk determination unit can be regarded as being a local, in time, detection system. The HF risk determination unit can be adapted to detect at least one of a presence of a PESP and a disturbed force-frequency relation based on a PPG which has been measured during or after a physical exercise of the subject like climbing a staircase. Moreover, the HF risk determination unit can be adapted to detect at least one of a presence of a PESP and a disturbed force-frequency relation based on a) a PPG which has been measured during or after a physical exercise of the subject like climbing a staircase and b) a PPG which has been measured while the subject was resting. In particular, a disturbed force-frequency relation can be detected by considering a first PPG or PPG wave, which has been measured in a rest state of the subject, and a second PPG or PPG wave, which has been measured in a non-rest state of the subject, wherein the first PPG or PPG wave has a smaller frequency than the second PPG or PPG wave due to the different activity levels and wherein a disturbance of the force-frequency relation can be detected based on a detection whether the peak values for the first PPG or PPG wave are smaller than the peak values for the second PPG or PPG wave.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or devices may fulfill the functions of several items recited in the claims. The mere fact that certain measures are recited in mutually different dependent claims does not indicate that a combination of these measures cannot be used to advantage.

Procedures like the determination of the breathing rate based on the PPG, the determination of the HF risk, et cetera performed by one or several units or devices can be performed by any other number of units or devices. These procedures and/or the control of the determination system for determining a HF risk for a subject in accordance with the determination method for determining a HF risk for a subject can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A determination system for determining a heart failure (HF) risk for a subject, wherein the determination system comprises:
   a photoplethysmogram providing unit for providing a photoplethysmogram of the subject; and
   a heart failure risk determination unit for determining the heart failure risk based on the provided photoplethysmogram, wherein the heart failure risk determination unit is adapted to:
      detect at least one of a presence of a postextrasystolic potentiation (PESP) and a disturbed force-frequency relation (FFR) based on the provided photoplethysmogram,
      determine peak values of peaks at different times, which are indicative of heights of peaks of a left ventricular pressure over time,
      determine frequency values for different times, which are indicative of a frequency of the left ventricular pressure over time, wherein the frequency values are defined by an inverse of temporal distances between consecutive ones of the peaks of the left ventricular pressure, for determining a temporal behavior of characteristics of the left ventricular pressure based on the photoplethysmogram,
      provide rules which include a frequency deviation threshold and which define the heart failure risk depending on whether a deviation between temporally consecutive frequency values is larger than the frequency deviation threshold, and
      determine the heart failure risk based on: (i) the detection of the at least one of the presence of the PESP and the disturbed FFR; (ii) the determined temporal behavior; and (iii) the provided rules, which include the frequency deviation threshold, and which define the heart failure risk depending on whether the deviation between temporally consecutive frequency values is larger than the frequency deviation threshold.

2. The determination system of claim 1, wherein providing the rules includes providing a first peak value threshold and a second peak value threshold, and wherein the heart failure risk determination unit is adapted to:
   detect the presence of the postextrasystolic potentiation as a case where (a) and (b) are both true, where (a) is true when a peak value is smaller than the first peak value threshold and wherein (b) is true when a following peak value is not larger than the second peak value threshold.

3. The determination system of claim 1, wherein the rules define the detection of the disturbed force frequency relation as detecting that the frequency values increase over time, while peak values which are indicative of heights of peaks of the left ventricular pressure do not increase over time, and wherein the heart failure risk is determined based on the rules.

4. The determination system of claim 1, further comprising an activity state providing unit for providing an indication of an activity state of the subject, wherein the rules include an activity frequency threshold that depends on the activity state, wherein the rules define the heart failure risk as depending on whether the frequency values are larger than the activity frequency threshold for a respective activity state, and wherein the heart failure risk is determined based on the rules.

5. The determination system of claim 1, further comprising a breathing rate providing unit for providing a breathing rate of the subject, wherein the HF risk determination unit is adapted to determine the HF risk based on the provided breathing rate.

6. The determination system of claim 5, further comprising an activity state providing unit for providing an indication of an activity state of the subject, wherein the HF risk determination unit is adapted to provide a breathing rate threshold that depends on the activity state and to determine the HF risk as depending on whether the breathing rate is larger than the breathing rate threshold for a respective activity state.

7. The determination system of claim 5, wherein the breathing rate providing unit is adapted to determine the breathing rate based on the photoplethysmogram and to provide the determined breathing rate.

8. The determination system of claim 1, wherein the heart failure risk determination unit is adapted to detect atrial fibrillation of the subject's heart based on the provided photoplethysmogram and to determine the heart failure risk based on the detection of the atrial fibrillation.

9. A method for determining a heart failure (HF) risk for a subject, wherein the method comprises:
   providing a photoplethysmogram of the subject by a photoplethysmogram providing unit; and
   ascertaining a heart failure risk based on the provided photoplethysmogram by:
      detecting at least one of a presence of a postextrasystolic potentiation and a disturbed force-frequency relation based on the provided photoplethysmogram,
      determining peak values of peaks at different times, which are indicative of heights of peaks of a left ventricular pressure over time,
      ascertaining frequency values for different times, which are indicative of a frequency of the left ventricular pressure over time and are defined by an inverse of temporal distances between consecutive ones of the peaks of the left ventricular pressure, for ascertaining a temporal behavior of characteristics of the left ventricular pressure based on the photoplethysmogram,
      providing rules which include a frequency deviation threshold and which define the heart failure risk depending on whether a deviation between temporally consecutive frequency values is larger than the frequency deviation threshold, and
      ascertaining the heart failure risk based on: (i) the detection of the at least one of the presence of the postextrasystolic potentiation and the disturbed force-frequency relation; (ii) the ascertained temporal behavior; and (iii) the provided rules, which include the frequency deviation threshold, and which define the heart failure risk depending on whether the deviation between temporally consecutive frequency values is larger than the frequency deviation threshold.

10. The determination system of claim 1, wherein the heart failure risk determination unit is adapted to assign the determined heart failure risk to one of at least two defined degrees of heart failure risk, including at least a first degree of heart failure risk and a second degree of heart failure risk which is greater than the first degree of heart failure risk, and wherein the determination system is configured to generate an optical, and/or acoustical, and/or tactile alarm when the heart failure risk determination unit assigns the heart failure risk to the second degree of heart failure risk.

11. The method of claim 9, further comprising:
assigning the determined heart failure risk to one of at least two defined degrees of heart failure risk, including at least a first degree of heart failure risk and a second degree of heart failure risk which is greater than the first degree of heart failure risk; and
generating an alarm when assigning of the determined heart failure risk reaches the second degree of heart failure risk.

12. The method of claim 9, wherein providing the rules includes providing a first peak value threshold and a second peak value threshold, and wherein the method comprises:
detecting the presence of the postextrasystolic potentiation as a case where (a) and (b) are both true, where (a) is true when a peak value is smaller than the first peak value threshold and wherein (b) is true when a following peak value is not larger than the second peak value threshold.

13. The method of claim 9, wherein the rules define the detection of the disturbed force frequency relation as detecting that the frequency values increase over time, while peak values which are indicative of heights of peaks of the left ventricular pressure do not increase over time.

14. The method of claim 9, comprising providing an indication of an activity state of the subject, wherein the rules include an activity frequency threshold that depends on the activity state and wherein the rules define the heart failure risk as depending on whether the frequency values are larger than the activity frequency threshold for a respective activity state.

15. The method of claim 9, comprising providing a breathing rate of the subject, and the HF risk is ascertained based on the provided breathing rate.

16. The method of claim 9, comprising providing an indication of an activity state of the subject, wherein the rules provide a breathing rate threshold that depends on the activity state, and the HF risk is ascertained as depending on whether the breathing rate is larger than the breathing rate threshold for the respective activity state.

17. The method of claim 9, comprising ascertaining a breathing rate based on the photoplethysmogram.

18. The determination system of claim 1, further comprising:
a casing enclosing the photoplethysmogram providing unit and the heart failure risk determination unit; and
a wrist band for holding the casing at a wrist of the subject,
wherein the heart failure risk determination unit is adapted to determine the HF risk without using measured baseline values of the FFR for the subject.

19. The method of claim 9,
wherein the photoplethysmogram (PPG) providing unit is comprised in a casing which is held to a wrist of the subject by a wrist band,
wherein providing the PPG of the subject comprises:
directing light into skin at the wrist of the subject;
detecting light from the skin at the wrist of the subject; and
generating the PPG based on the detected light, and
wherein ascertaining the heart failure risk is performed without using baseline values of the FFR for the subject.

20. The determination system of claim 1, wherein the determination of the heart failure risk is further based on: currently measured photoplethysmogram signals without using baseline values.

21. The method of claim 9, wherein the ascertaining the heart failure risk is further based on currently measured photoplethysmogram signals without using baseline values.

22. A tangible, non-transitory computer readable medium that stores instructions, which when executed by a processor, cause the processor to:
detect at least one of a presence of a postextrasystolic potentiation (PESP) and a disturbed force-frequency relation (FFR) based on a provided photoplethysmogram,
determine peak values of peaks at different times, which are indicative of heights of peaks of a left ventricular pressure over time,
determine frequency values for different times, which are indicative of a frequency of the left ventricular pressure over time and defined by an inverse of temporal distances between consecutive ones of the peaks of the left ventricular pressure, for determining a temporal behavior of characteristics of the left ventricular pressure based on the photoplethysmogram,
provide rules which include a frequency deviation threshold and which define a heart failure risk depending on whether a deviation between temporally consecutive frequency values is larger than the frequency deviation threshold, and
determine a heart failure risk based on: (i) the detection of the at least one of the presence of the PESP and the disturbed FFR; (ii) the determined temporal behavior; and (iii) the provided rules, which include the frequency deviation threshold, and which define the heart failure risk depending on whether the deviation between temporally consecutive frequency values is larger than the frequency deviation threshold.

* * * * *